(12) United States Patent
Glocker

(10) Patent No.: US 11,439,755 B2
(45) Date of Patent: Sep. 13, 2022

(54) MEDICATION CONTAINER HAVING AN END PLUG, USE OF A PLUG-SECURING PART TO SECURE AN END PLUG IN A MEDICATION CONTAINER AND PLUG-SECURING PART

(71) Applicant: VETTER PHARMA-FERTIGUNG GMBH & CO. KG, Ravensburg (DE)

(72) Inventor: Joachim Glocker, Weingarten (DE)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 337 days.

(21) Appl. No.: 16/613,260

(22) PCT Filed: Apr. 27, 2018

(86) PCT No.: PCT/EP2018/060972
§ 371 (c)(1),
(2) Date: Nov. 13, 2019

(87) PCT Pub. No.: WO2018/210556
PCT Pub. Date: Nov. 22, 2018

(65) Prior Publication Data
US 2021/0162129 A1       Jun. 3, 2021

(30) Foreign Application Priority Data

May 16, 2017   (DE) ..................... 10 2017 208 255.0

(51) Int. Cl.
*A61M 5/19*          (2006.01)
*A61J 1/06*          (2006.01)
(Continued)

(52) U.S. Cl.
CPC ............... *A61M 5/19* (2013.01); *A61J 1/062* (2013.01); *A61J 1/1406* (2013.01); *A61J 1/16* (2013.01);
(Continued)

(58) Field of Classification Search
CPC .................. A61M 5/19; A61M 5/2448; A61M 2005/3106; A61M 5/24; A61J 1/062; A61J 1/16
See application file for complete search history.

(56) References Cited

U.S. PATENT DOCUMENTS 4,968,299 A  *  11/1990 Ahlstrand ......... A61M 5/31525
                                                           604/90
2012/0078171 A1    3/2012 Seiferlein et al.
(Continued)

FOREIGN PATENT DOCUMENTS

JP       H02-037647 U       3/1990
JP       H05-74544          10/1993
(Continued)

OTHER PUBLICATIONS

International Search Report (in English and German) and Written Opinion (in German) issued in PCT/EP2018/060972, dated Jun. 25, 2018; ISA/EP.
(Continued)

*Primary Examiner* — Bradley J Osinski
(74) *Attorney, Agent, or Firm* — Harness, Dickey & Pierce, P.L.C.; Stephen T. Olson

(57) ABSTRACT

A medicament container for a syringe or carpule has a base body surrounding an interior at least in sections. The base body has a central axis and a proximal opening. An end plug is arranged in the interior such that the end plug in the interior is displaceable along the central axis and separates a first proximal region of the interior from a second distal region of the interior. A plug securing part is at least partially insertable into the second region through the proximal opening. When inserted into the interior, the plug securing part is arranged closer to the proximal opening than the end
(Continued)

plug and is fixedly held in the interior by the positive and/or non-positive connection at least in a holding area.

20 Claims, 1 Drawing Sheet

(51) Int. Cl.
- *A61J 1/14* (2006.01)
- *A61J 1/16* (2006.01)
- *A61M 5/24* (2006.01)
- *A61M 5/00* (2006.01)
- *A61M 5/31* (2006.01)

(52) U.S. Cl.
CPC .......... *A61M 5/002* (2013.01); *A61M 5/2448* (2013.01); *A61M 5/2466* (2013.01); *A61M 2005/3106* (2013.01); *A61M 2005/3121* (2013.01)

(56) References Cited

U.S. PATENT DOCUMENTS

| | | | |
|---|---|---|---|
| 2012/0118139 A1 | 5/2012 | Seiferlein et al. | |
| 2016/0184522 A1 | 6/2016 | Horiuchi et al. | |
| 2019/0355463 A1* | 11/2019 | Gardner | G16H 40/63 |

FOREIGN PATENT DOCUMENTS

| | | |
|---|---|---|
| JP | H05-305140 A | 11/1993 |
| JP | 2006-271461 A | 10/2006 |
| KR | 100988221 B1 | 10/2010 |
| RU | 176780 U1 | 1/2018 |

OTHER PUBLICATIONS

Office Action received for the Russian Application No. RU2019139242, dated Jun. 7, 2021, 4 pages (2 pages of English translation and 2 pages of Official document).

International Preliminary Report On Patentability Chapter I and Written Opinion dated Nov. 28, 2019 in corresponding PCT Application No. PCT/EP2018/060972.

Office Action for JP 2019-563450, dated Nov. 24, 2021.

* cited by examiner

MEDICATION CONTAINER HAVING AN END PLUG, USE OF A PLUG-SECURING PART TO SECURE AN END PLUG IN A MEDICATION CONTAINER AND PLUG-SECURING PART

CROSSREFERENCE TO RELATED APPLICATIONS

This application is a 371 U.S. National Phase of International Application No. PCT/EP2018/060972, filed Apr. 27, 2018, which claims the benefit of German Patent Application No. 10 2017 208 255.0, filed May 16, 2017. The entire disclosures of the above applications are incorporated herein by reference.

The invention relates to a medicament container having an end plug, a use of a plug securing part for securing an end plug in a medicament container and a plug securing part.

Plug securing parts, medicament containers with end plugs and the use of the plug securing part for securing the end plug in the medicament container are known. The plug is traditionally secured in syringes by a finger rest with an integrated plug securing part. Even for dual-chamber syringes, such a securing by means of the finger rest is known. Carpules, however, in particular dual-chamber carpules, usually do not have a finger rest. Therefore, the plug in carpules is traditionally secured by mounting the carpule in an application device, particularly a disposable pen, such that a piston rod of the application device secures the end plug.

In addition, transport boxes for accommodating a plurality of carpules are known to secure the end plug, in particular during an air transport, and hold it in position. For this purpose, elevations are provided in the bottom of the transport box, which penetrate into the main body of the medicament container in order to secure an end plug arranged therein. The medicament container in such a transport box is thus traditionally arranged between the bottom and the lid of the transport box while the elevation that begins at the bottom penetrates into the interior of the body of the medicament container to limit a displacement of the end plug arranged there in the direction of the bottom during transport.

A disadvantage of this known prior art is that a securing of the end plug by means of a finger rest is only possible if the medicament container has such a finger rest. Securing the end plug by mounting the carpule in an application device, however, is cumbersome and expensive. Securing the end plug by means of a transport box has the disadvantage that the elevation in the bottom of the box must be matched exactly to the position of the end plug in the medicament container along a central axis of the end plug. Thus, only a medicament container, or a set of medicament containers with positions of the end plug that exactly correspond to the length of the elevation can be reliably secured in a transport box. Such transport boxes are also large and inefficient when trying to secure small amounts of medicament containers with individually different end plug positions along the central axes of the medicament containers.

Due to the systems used, the filling of medicament containers is associated with air pockets in the chambers to be filled. Especially in dual-chamber carpules, the amount of air in the entire filling volume is comparatively large. Such air pockets cause a force to act on the plugs delimiting the chambers, in particular on the end plug, when the medicament container and thus the end plug is subjected to negative pressure or a vacuum. Consequently, it is possible that the end plug is displaced, in particular during a transportation of medicament containers associated with changes in elevation, in particular during air transport or during transport in a mountain region. The pressure gradient occurring during transport between a closed area of the medicament container and the outside air can thus lead to a displacement of the end plug, in particular in the direction of a proximal end of the medicament container. As a result, a medically sterile area is contaminated or at least exposed to the risk of contamination.

The object of the invention is to provide a medicament container, a use of a plug securing part and a plug securing part with said disadvantages being avoided.

The object is achieved by providing the objects in the independent claims. Advantageous embodiments are described in the dependent claims.

The object is achieved, in particular, by providing a medicament container, in particular a syringe or carpule, particularly preferably a dual-chamber syringe or a dual-chamber carpule with a base body, wherein the base body encloses an interior at least in sections, wherein the base body has a central axis and a proximal opening, wherein an end plug is arranged in the interior space such that the end plug is displaceable in the interior space along the central axis and separates a first, with respect to the end plug, distal region of the interior from a second, with respect to the end plug, proximal region of the interior. The medicament container is characterized in that a plug securing part is provided, which is at least partially insertable into the second region of the interior through the proximal opening, wherein the plug securing part, when inserted into the interior, is arranged closer to the proximal opening than the end plug and is fixedly held in the interior by the positive and/or non-positive connection at least in a holding area. The base body preferably has a rotationally symmetrical, particularly preferably a cylindrical shape and encloses the interior, which is at least partially adapted to be filled with a medicinal agent and/or excipient. Together with the end plug and, if appropriate, further plugs or other closure elements, the base body completely encloses at least part of the interior. The base body also preferably has at least one further, closable opening. However, the main body particularly preferably has only the proximal opening and exactly one more closable distal opening. Below, it is assumed that all other closable openings are closed.

In such a medicament container, the end plug is securely held in the medicament container. A displacement of the end plug from the medicament container through the proximal opening is preventable by the plug securing part and prevented in the inserted state. In addition, the plug securing part of such a medicament container can be inserted and removed in a simple manner, in particular manually.

Due to the fact that the end plug is in close contact with an inner wall of the interior, the end plug separates the first region from the second region. Due to this separation, a purity and/or sterility of the first region is ensured. The first region thus forms a closed space when the end plug is arranged as intended. Preferably, the first region is divided into two separate chambers by means of at least one further plug, in particular a center plug. The medicament container thus forms a dual-chamber system, in particular a dual-chamber carpule or a dual-chamber syringe.

The first region is configured to receive a medicinal agent and/or excipient. In addition, the main body, the end plug and all other openings are configured to seal the first region against external contaminants. The second region, on the other hand, is not necessarily sealed. Rather, an application device may act on the end plug via the second region in order to displace the end plug in the direction of the distal end and to thus produce a medicinal agent and/or excipient stored in the medicament container from the medicament container. The second region thus has fluidic contact with the surroundings of the medicament container via the proximal opening of the main body. Consequently, the second region is not sterile and is not protected from contamination.

Due to the arrangement of the end plug and the first region as well as the second region described here, the first region is farther from the proximal opening of the main body than the second region.

The plug securing part is at least partially insertable, preferably inserted, through the proximal opening into the second region of the interior and—in the inserted state—can be removed from the second region of the interior through the proximal opening. In addition, the plug securing part is—in the inserted state—displaceable along the central axis and preferably rotationally symmetrical, more preferably mounted rotationally symmetrical to the central axis. In addition, the plug securing part is preferably connected with the inner wall or an outer wall of the base body by a positive and/or non-positive connection and thus held in the interior in a fixed position. Preferably, the plug securing part is alternatively or additionally held in the interior in a fixed position by a positive and/or non-positive connection by means of an outer structure and/or an element engaging in the base body, in particular a transport container.

According to one embodiment of the invention, the plug securing part is held in such a positionally fixed position and/or arranged relative to the end plug that a particularly pressure-induced displacement of the end plug in the proximal direction is limited by the plug securing part. In particular, therefore, a displacement of the end plug out of the medicament container is prevented and limited by the abutment of the proximal end of the end plug against the distal end of the plug securing part.

Particularly preferably, the plug securing part directly adjoins the end plug in the inserted state so that any displacement of the end plug in the direction of the proximal opening is prevented.

Thus, a displacement of the end plug that impairs the sterility of the first region of the interior in the direction of the proximal opening is preferably prevented by the positionally stable plug securing part. The sterility of the first region of the interior is particularly at risk when the end plug is completely displaced into the second region of the interior. Preferably, the displacement of the end plug in the proximal direction is thus limited by the plug securing part so that the end plug is not fully displaceable into the second region. This is particularly ensured when the distal end of the plug securing part is arranged at a distance from the proximal end of the end plug, this distance being smaller than the axial length of the end plug. Advantageously, the sterility of the first region is thus ensured in a particularly reliable manner. It is also possible, however, that the proximal end of the end plug rests against the distal end of the plug securing part.

According to one embodiment of the invention, the plug securing part interacts with the inner wall of the base body in a positive and/or non-positive connection. Such a positive and/or non-positive connection is particularly easy to establish and, compared with a positive or non-positive connection between the plug securing part and an outer wall, less prone to failure.

According to one embodiment of the invention, the plug securing part has an elastic holding means with an elasticity that is preferably at least radially acting to the central axis, wherein the elastic holding means is configured to press the plug securing part when inserted into the interior, against the body, preferably the inner wall of the body in a non-positive connection. By means of such an elastic holding means, the plug securing part is held in a fixed position in the interior, at least in the holding area, in a non-positive connection. Preferably, a positive connection is made possible by means of the elastic holding means wherein the elastic holding means is guided through a radial taper of the second region and widens behind the radial taper due to its elasticity and thus engages behind the taper. The medicament container having such a plug securing part has the advantage that the securing of the end plug by means of the elastic holding means is easy to perform and that the insertion and removal of such a plug securing part into and out of the second region is therefore particularly easy to perform, in particular manually and quickly.

According to one preferred embodiment, the elastic holding means comprises a spring, and/or a spring-like structure, and/or a spring-like element, and/or a vulcanized elastomer, preferably rubber, and/or a material weakening zone, preferably a recess into which adjoining material, preferably—perpendicular to the central axis—outside adjacent material, can be elastically deformed. A material weakening zone is understood here to mean a region with material which, when force is applied, is flexible and/or compressible relative to the material surrounding the material weakening zone. The material weakening zone is thus compressed more strongly when force is applied than the material surrounding the material weakening zone. Alternatively or additionally, the material weakening zone comprises a liquid and/or a gas, in particular air, wherein the gas and/or the liquid of the material weakening zone can be displaced out of the material weakening zone when force is applied. Preferably, the elastic holding means has a recess. The plug securing part with such an elastic holding means can be produced in a particularly cost-effective manner and/or in one piece and/or from the same material.

According to one embodiment of the invention, the plug securing part has a round, cross-shaped or i-shaped cross section at least in a distal region of the plug securing part. A particularly favorable distribution of forces for realizing the non-positive connection is provided by such a cross-section in the distal region of the plug securing part, i.e. the region which precedes the insertion of the plug securing part into the second region of the medicament container. Thus, webbing located opposite the central axis, which forms the cross-shaped or i-shaped cross-section, and/or the regions that are opposite the central axis and that form the round cross-section preferably stabilize each other in an exact manner if the elastic holding means, when inserted into the plug securing part, is arranged and compressed in this distal region. Thus, the radially acting forces providing the non-positive connection are locally maximized, and any deviating force components avoided. Furthermore, such a cross section preferably ensures that the plug securing part is permeable to air at least in the distal region, preferably in the entire region of the plug securing part, which penetrates into the second region so that a tight closure of the region between the plug securing part and the end plug is avoided when the plug securing part is inserted into the medicament container. This makes it possible for the pressure, in particular the air pressure between the plug securing part and the end plug, to be increased or decreased, in particular, during the insertion or the removal of the plug securing part. This way, an unintentional displacement of the end plug in the distal and/or proximal direction is avoided.

According to an embodiment of the invention, the plug securing part has a stop structure, in particular at its proximal end, wherein the plug securing part has at least a radial extension in the region of the stop structure in the inserted state perpendicular to the central axis, which is at least greater than a minimum, but preferably greater than a maximum radial extension of the proximal opening of the body, so that an insertion depth of the plug securing member is limited in the medicament container by the abutment of the plug structure against the medicament container. The stop structure is preferably arranged at the edges of the plug securing part, i.e. in the inserted state, at a radial distance from the central axis of the base body, in particular on a lateral surface of the plug securing part. Preferably, the stop structure is formed as a thickening or projection with respect to the lateral surface. Particularly preferably, the stop structure is integrally formed with the plug securing part and/or made from the same material.

If the at least one radial extension of the plug securing part is at least greater than the minimum radial extension of the proximal opening of the main body, then there is at least one rotational position around the central axis in which the stop structure, in the inserted state, abuts against the proximal end of the medicament container and thus prevents any further penetration of the plug securing part into the medicament container. Preferably, however, the at least one radial extension of the plug securing part is greater than the maximum radial extension of the proximal opening of the base body so that the insertion depth is limited in each rotational position of the plug securing part by abutment of the stop structure at the proximal end of the medicament container.

In any event, the stop structure is arranged at an axial distance from the distal end of the plug securing part that is less than or equal to an axial distance between the proximal end of the end plug and the proximal opening of the base body. Such a medicament container has the advantage that the end plug arranged therein cannot be displaced, in particular not by means of the plug securing part. Thus, the safety of the medicament container and a medicinal agent and/or excipient in it is increased.

According to one embodiment of the invention, a grip section is formed on a proximal end of the plug securing part when the plug securing part is inserted with said grip section comprising an undercut structure and/or material that is easy to grasp and/or a rough surface structure. Material that is easy to grasp refers here, in particular, to non-slip material, and/or a material with static friction that is higher than that of other material used for the plug securing part, and/or a rubber, and/or rubbery material. Such a grip area makes it easier to handle the medicament container. The plug securing part of the medicament container can therefore be inserted and removed in a particularly simple and fast and especially manual manner.

According to one embodiment of the invention, the medicament container has a safety indicator, preferably a label or a shrinkable sleeve. The safety indicator, when inserted into the plug securing part, is preferably arranged in a region in which the plug securing part adjoins the base body on the body base and the plug securing part so that the safety indicator can be changed, preferably damaged or at least partially removed by a displacement of the plug securing part. The safety indicator preferably has a predetermined breaking point, in particular a perforation. Such a safety indicator makes it possible to detect preferably visually whether a displacement of the plug securing part has taken place. In particular, in the event of pressure-induced displacements as they take place during transport, a sterility-compromising displacement of the end plug and/or the plug securing part is often not detectable in retrospect since the end plug is moved back to its original position when the outside air pressure returns to its initial level. A preferably only temporary displacement of the plug securing part and/or the end plug can be detected later by means of a safety indicator of the type described here. The safety indicator described here is irreversibly manipulated in the event of a displacement of the plug securing part, in particular an impairment of the sterility, in such a way that it does not return to its initial state when the end plug returns to its original position. Thus, a temporary displacement would be noticed. This increases the safety of the medicament container, in particular a medicament container filled with a drug. In the exemplary embodiment of a medicament container with a safety indicator described here, the plug securing part is, when inserted, preferably arranged directly adjacent to the end plug so that it can be reliably closed by means of the safety indicator to prevent a displacement of the end plug, at least in the proximal direction.

According to one embodiment of the invention, the plug securing part comprises polypropylene, polystyrene and/or at least one resin. Preferably, the plug securing part is manufactured in a plastic injection molding process. A medicament container with such a plug securing part has the advantage that it is particularly cost-effective.

According to an embodiment of the invention, the plug securing part has a mechanically, preferably non-contact, particularly preferably electromagnetically readable information carrier, in particular an RFID chip. By means of such an information carrier, it is possible to individually record and store content-specific and/or transport-specific and/or origin-specific information about the medicament container and/or its content in a particularly cost-effective manner. Consequently, such information can be stored and retrieved fast as well as better attributable to the medicament container and/or its contents.

According to embodiment of the invention, the plug securing part is shaped such that—in the inserted state—it does not cover any outer peripheral surface of the medicament container. Consequently, information attached to the outer peripheral surface is recognizable and the handling of the medicament container is improved.

According to a preferred embodiment, the plug securing part of the medicament container is colored, in particular monochrome or multicolored, white or black and/or provided with a pattern or mark. This design of the plug securing part is preferably a coding by means of which at least one piece of information, in particular information pertaining to the medicament, medicament dosage and/or medicament configuration, is associated with such optical characteristics, i.e. color, pattern and/or characters. A medicament configuration is understood, in particular, as a composition of various active ingredients and/or excipients.

The invention also includes a set or an assortment of medicament containers according to one of the embodiments described above, wherein each medicament container is associated with a respective plug protection part, which is colored, especially monochrome or multi-colored, white or black, and/or provided with a pattern or sign.

Due to the colored design of the plug securing parts and/or their pattern or characters, the various medicament containers of the set or the assortment are optically marked, wherein the respective marking, i.e. the color, the pattern and/or the character, is associated with certain information about the medicament container, for example, information about a medicament in the medicament container, a medicament dosage and/or a medicament configuration. The position of the end plug may vary depending, in particular, on the medicament contained in the medicament container and/or the medicament configuration. Correspondingly, the plug securing parts associated with the medicament container preferably have different lengths so that they can reach the respective position in the second region through the proximal opening as closely as possible. This varying length of the plug securing parts is preferably coded—alternatively or additionally—by the color, the pattern and/or the character.

If, in particular, there is a set of medicament containers in which each medicament container has different plug securing parts, such encoded information can be detected by an optical control and associated with the respective medicament container. Particularly preferably, such information is also associated with the length along the central axis of the plug securing part.

More preferably, the length of each plug securing part is adjusted to the position of the corresponding end plug in the medicament container in the set of medicament containers so that the respective plug securing parts abut directly against the corresponding end plug. Thus, it is possible to secure each individual end plug in a set of medicament containers with the same basic bodies but different end plug positions in a reliable and individualized manner.

The invention also includes a set or an assortment of plug securing parts, which are colored, in particular monochrome or multicolored, white or black, and/or provided with a pattern or mark. At least two of the plug securing parts differ from each other in this case with respect to the color, the pattern and/or the character, wherein different information is associated with the different colors, patterns and/or characters, in particular according to a coding, wherein the information preferably pertains to a medicament contained in a medicament container to be secured by the respective plug securing part, a medicament dosage and/or a medicament configuration.

The object is also achieved, in particular, by providing a transport container for at least one medicament container, which has at least one receptacle for the at least one medicament container, wherein the receptacle has a length which corresponds to an axial length along the central axis of the medicament container with the plug securing part inserted. Thus, the medicament container can be stored in the receptacle of the transport container without any play, at least in the direction of its length. Preferably, a medicament container stored in the transport container can also be stored without play perpendicular to the central axis. If the transport container has several receptacles, it is advantageously possible to reliably store a plurality of medicament containers, even if they have different end plug positions, along the central axis and appropriately associated plug securing parts without endangering the safety of the medicament container and/or the sterility in the first region. In particular, each receptacle of the medicament container may have the same length. By adapting the plug securing parts, it is possible to arrange a set of medicament containers in the transport container, the set having at least two medicament containers with each having different end plug positions.

The object is furthermore achieved, in particular, by providing a plug securing part for use in a medicament container for securing an end plug. The medicament container is preferably designed according to one of the preceding embodiments. The invention calls for a medicament container with a base body, which at least partially encloses an interior, a central axis and a proximal opening, wherein and end plus is arranged in the interior such that the end plug is displaceable in the interior along the central axis and separates a first, with respect to the end plug, distal region of the interior from a second, with respect to the end plug, proximal region of the interior. The use of the plug securing part is characterized in that the plug securing part is inserted into the second region through the proximal opening so that it is positioned closer to the proximal opening than the end plug, wherein the plug securing part is held at least in a holding area of the second proximal region of the medicament container by means of a positive and/or non-positive connection. This leads to the advantages already mentioned above with regard to the medicament container. The end plug is, in particular, reliably held in a medicament container when using the plug securing part in such a way.

According to one embodiment of the use, the displacement of the end plug is limited by the plug securing part, preferably in such a way that the sterility of the first region of the interior is ensured. The displacement of the end plug is limited, in particular in the proximal direction, by the abutment of the proximal end of the end plug against the distal end of the plug securing part.

The object is achieved as well by providing a plug securing part, which is configured for use in a medicament container according to one of the embodiments described above. This results in the advantages mentioned above.

It is found overall that an end plug is held in a particularly reliable manner in a medicament container with the medicament container shown here, the transport container, the plug securing part and the use of the plug securing part in a medicament container.

The invention will be explained in more detail below with reference to the drawings. In the figures.

Figure 1:
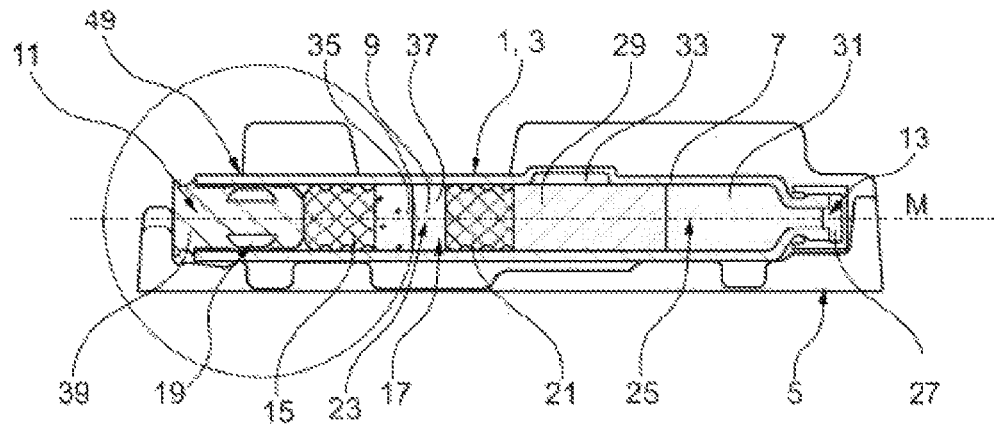
FIG. 1 shows a side view of an exemplary embodiment of a medicament container.

FIG. 1 shows an embodiment of a medicament container 1, in this case a dual-chamber carpule 3, in a longitudinal section. The medicament container 1 is stored along a central axis M without any play in a transport container 5. The medicament container 1 comprises a main body 7, which encloses an interior 9 substantially in the form of a cylinder, the central axis M and a proximal opening 11 as well as a distal opening 13. An end plug 15 is arranged in the interior 9 of the main body 7 such that this end plug 15 is displaceable in the interior 9 along the central axis M and separates a first, with respect to the end plug, distal region 17 from a second, with respect to the end plug, proximal region 19 of the interior 9. The first region 17 is divided hereby into a first chamber 23 and a second chamber 25 by means of a center plug 21.

The distal opening 13 is closed by a closure element 27 so that the second chamber 25 forms a closed space, which is delimited by the main body 7, the center plug 21 and the closure element 27. A lyophilisate 29, which is essentially surrounded by air 31, is stored inside the second chamber 25. A bypass 33 is formed in the main body 7 in the area of the second chamber 25 as well. Subsequent to a displacement of the center plug 21 in the direction of the distal opening along the central axis M, this allows for a mixing of the contents of the two chambers 23, 25.

The first chamber 23 comprises a solvent 35 and an air bubble 37. The first chamber forms a closed space, which is delimited by the center plug 21, the base body 7 and the end plug 15. After the distal opening 13 has been opened, it is, by means of an application device, which is not shown here, possible to displace the end plug 15 and, at the same time, the center plug 21 in the direction of the distal opening 13. If the center plug 21 arrives in the axial section of the bypass 33, the contents of the first chamber 23, i.e. especially the solvent 35, is transferred into the second chamber 25. This makes it possible to mix the contents of the two chambers. If the end plug 15 is displaced further in the direction of the distal opening 13 by means of the application device, the mixed contents of the second chamber 25 is discharged from the interior 9 via the distal opening 13.

In the exemplary embodiment shown here, a plug securing part 39 is arranged in the second region 19 such that the end of the end plug 15 facing the proximal opening 11 directly adjoins the end of the plug securing part 39 facing the distal opening 13. Thus, an action on the end plug 15 via the proximal opening 11, in particular by means of an application device, is not possible here, and the end plug is therefore protected against such action and an associated displacement in the direction of the distal opening 13.

Figure 2:
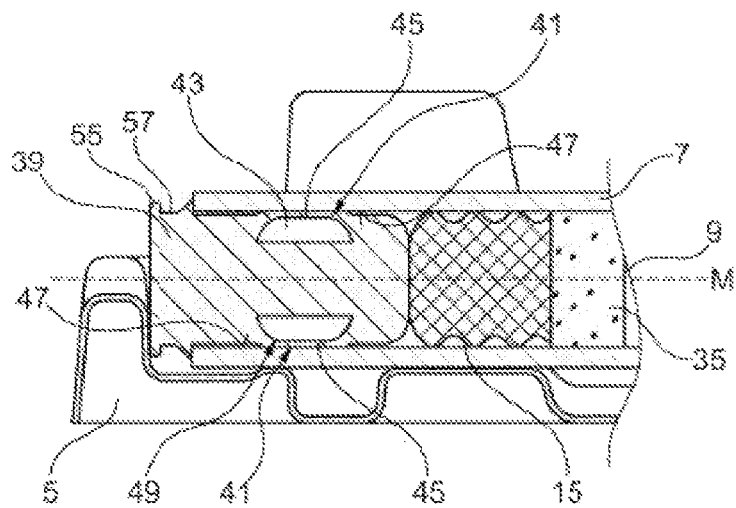
FIG. 2 shows an enlarged view of the proximal end of the medicament container according to the embodiment of FIG. 1.

FIG. 2 shows an enlarged view of the proximal region of the medicament container 1 according to FIG. 1. Identical elements and elements with the same function are provided with the same reference signs so that reference is made to the description above in this regard.

FIG. 2 makes clear that the plug securing part 39 is held in the second region 19 of the interior 9 by a non-positive connection by means of at least one elastic holding means 41, in this case a plurality of elastic holding means 41. The at least one elastic holding means 41 has a material weakening zone 43, which is formed here as a recess. Adjoining the material weakening zone 43 on the outside, viewed in the radial direction, is a web-shaped structure 45 of the plug securing part 39, which has elastic properties.

When plug securing part 39 shown here is in its inserted state, the web-shaped structure 45 is elastically deformed into the material weakening zone 43 so that a spring force acts on the inside wall 47 of the base body 7 from the inside and holds the plug securing part 39 in a non-positive connection in a holding area 49 of the interior 9.

Figure 3:
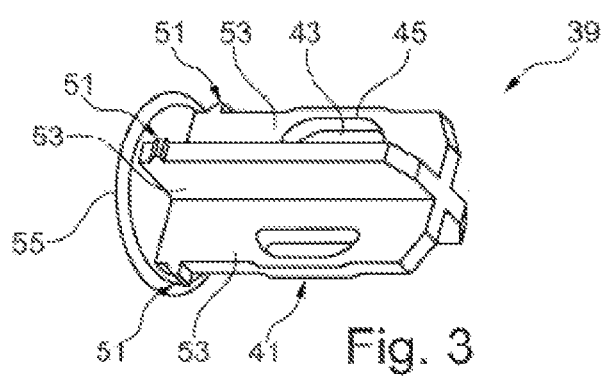
FIG. 3 is a perspective view of a plug securing part according to FIGS. 1 and 2.

FIG. 3 shows a perspective view of the plug securing part 39 according to FIGS. 1 and 2. In this illustration, the plug securing part 39 has a cross-shaped cross-section with two diametrically opposed elastic holding means 41. Starting from the distal end, this cross-shaped cross section extends across a large region of the plug securing part 39, in particular over the distal region, which, in the inserted state, is arranged in the second region 19 of the base body 7.

In FIG. 3, the plug securing part 39 is not in the inserted state so that the elastic holding means 41 is relaxed, and no mechanical stress energy is stored therein. Thus, the web-shaped structure 45 projects in the radial direction, i.e. perpendicular to the central axis M, with respect to the regions adjacent to the web-shaped structure 45. By inserting this plug securing part 39 into a medicament container 1 with a cylindrical interior 9, these web-shaped structures 45 are radially deformed inward in the direction of the center axis M into the material weakening zone 43.

Furthermore, it can be seen in FIG. 3 that the plug securing part 39 has a stop structure 51 in its rear distal region, which, in the inserted state of the plug securing part 39, faces away from the distal opening 13. FIG. 3 shows three stop structures 51 with a fourth stop structure 51 being arranged on the side facing away from the observer. Each of the stop structures 51 is formed as a projecting step on one of four webs 53, which are perpendicular to each other and form the cross-shaped cross-section. In each case, two of the stop structures 51, which are arranged opposite each other, span across a width that is greater than a diameter of the proximal opening 11 of the medicament container 1. In particular, each stop structure 51 in the plug securing part 39 shown here has a radial extension in the inserted state that is perpendicular to the central axis 11 that is greater than a radius of the proximal opening 11 of the medicament container 1. This prevents the plug securing part 39 from being inserted too far into the medicament container 1 when inserted into the medicament container 1. This prevents the end plug 15 from being displaced from its intended position in the direction of the distal opening 13 by means of the plug securing part 39.

In a particularly preferred embodiment of the plug securing part 39 of the medicament container 1, the distance between the protruding step of the stop structure 51 and the distal end of the plug securing part 39 is adapted to the axial position of the end plug 15 in the medicament container 1 such that the plug securing part 39 abuts, in the inserted state, with the stop structure 51 against the proximal end of the medicament container 1 with the distal end of the plug securing part 39 being immediately adjacent to the proximal end of the end plug 15 without the end plug 15 being displaced from its original position by the insertion of the plug securing part 39.

A grip section 55 is formed at the proximal end of the plug securing part 39 as well, which is particularly clearly visible in FIG. 3. The grip section 55 is formed here by a round grip plate, which starting from the proximal end has an undercut structure 57, which can be seen particularly well in FIG. 2. This makes it particularly easy to grab the plug securing part 39 in the inserted state, especially manually, to remove it from the medicament container 1.

Overall, it is found that the medicament container 1, the plug securing part 39 and the use of the plug securing part 39 in the medicament container 1 proposed here provide a particularly reliable and versatile securing of an end plug 15 in a medicament container 1 that is customizable on a medicament container 1.

The invention claimed is:

1. A medicament container, the medicament container comprising:
    a base body that at least partially surrounds an interior, the base body having a central axis and a proximal opening, wherein the medicament container forms a dual chamber system; and
    an end plug arranged in the interior and displaceable along the central axis, the end plug separates a first region of the interior from a second region of the interior, the first region being a distal region of the interior with respect to the end plug, the second region being proximal region of the interior with respect to the end plug, the medicament container including a plug securing part insertable at least partially into the second region of the interior through the proximal opening, the plug securing part, when inserted into the interior, being closer to the proximal opening than the end plug, and held, at least in a holding area, in a fixed position in the interior by a connection selected from a positive connection, a non-positive connection and a combination thereof, wherein the plug securing part has at least one elastic holding element with an elasticity that acts on the central axis at least radially, wherein the elastic holding element is configured to hold the plug securing part, when inserted into the interior, onto the base body.

2. The medicament container according to claim 1, wherein the plug securing part is arranged in such a fixed position and/or relative to the end plug that a displacement of the end plug is limited in a proximal direction by the plug securing part.

3. The medicament container according to claim 1, wherein the plug securing part interacts with an inner wall of the base body in a positive manner and/or non-positive manner.

4. The medicament container according to claim 1, wherein, the elastic holding element is configured to hold plug onto an inner wall of the base body.

5. The medicament container according to claim 1, wherein the elastic holding element is selected from a group consisting of:
 a) a spring;
 b) a vulcanized elastomer;
 c) a material weakening zone; and
 d) combinations thereof.

6. The medicament container according to claim 1, wherein the elastic holding element includes a recess into material adjoining an outside perpendicular to the central axis is elastically deformable.

7. The medicament container according to claim 1, wherein the plug securing part comprises, at least in a distal region of the plug securing part one of a round, cross-shaped and i-shaped cross-section.

8. The medicament container according to claim 1, wherein the plug securing part has a stop structure, wherein the plug securing part comprises, in a region of the stop structure, at least a radial extension in an inserted state perpendicular to a central axis which is at least greater than a minimum but preferably greater than a maximum radial extension of the proximal opening of the base body so that an insertion depth of the plug securing part into the medicament container is limited by abutment of the stop structure against the medicament container.

9. The medicament container according to claim 1, wherein a grip section is formed at a proximal end of the plug securing part, when inserted, which comprises at least one of:
 a) an undercut structure;
 b) material that is easy to grasp; and
 c) a rough surface structure.

10. The medicament container according to claim 1, wherein the medicament container has a safety indicator, which, in an inserted state of the plug securing part, is arranged in one area in which the plug securing part adjoins the base body, on the base body and on the plug securing part in such a way that the safety indicator is altered by a displacement of the plug securing part.

11. The medicament container according to claim 10, wherein the safety indicator is selected from a label and a shrinkable sleeve.

12. The medicament container according to claim 10, wherein the safety indicator is damaged or at least partially removed by a displacement of the plug securing part.

13. The medicament container according to claim 1, wherein the plug securing part comprises polypropylene, polystyrene and/or at least one resin.

14. The medicament container according to claim 1, wherein the plug securing part has an RFID chip.

15. The medicament container according to claim 1, wherein the plug securing part is shaped such that, when inserted, it does not cover any outer peripheral surface of the medicament container.

16. A method of using the plug securing part for securing the end plug in the medicament container according to claim 1, wherein the plug securing the part is inserted into the second region through the proximal opening so that it is positioned closer to the proximal opening than the end plug, wherein the plug securing part is held at least in a holding area of the second region of the medicament container by a positive connection and/or non-positive connection.

17. The method according to claim 16, wherein the displacement of the end plug is limited by the plug securing part such that a sterility of the first region of the interior is ensured.

18. A medicament container, the medicament container comprising:
 a base body that at least partially surrounds an interior, the base body having a central axis and a proximal opening, wherein the medicament container forms a dual chamber system; and
 an end plug arranged in the interior and displaceable along the central axis, the end plug separates a first region of the interior from a second region of the interior, the first region being a distal region of the interior with respect to the end plug, the second region being a proximal region of the interior with respect to the end plug, the medicament container including a plug securing part insertable at least partially into the second region of the interior through the proximal opening, the plug securing part, when inserted into the interior, being closer to the proximal opening than the end plug, and held, at least in a holding area, in a fixed position in the interior by a connection selected from a positive connection, a non-positive connection and a combination thereof,
 wherein the medicament container has a safety indicator, which, in an inserted state of the plug securing part, is arranged in one area in which the plug securing part adjoins the base body, on the base body and on the plug securing part in such a way that the safety indicator is altered by a displacement of the plug securing part.

19. A medicament container, the medicament container comprising:
 a base body that at least partially surrounds an interior, the base body having a central axis and a proximal opening, wherein the medicament container forms a dual chamber system; and
 an end plug arranged in the interior and displaceable along the central axis, the end plug separates a first region of the interior from a second region of the interior, the first region being a distal region of the interior with respect to the end plug, the second region being a proximal region of the interior with respect to the end plug, the medicament container including a plug securing part insertable at least partially into the second region of the interior through the proximal opening, the plug securing part, when inserted into the interior, being closer to the proximal opening than the end plug, and held, at least in a holding area, in a fixed position in the interior by a connection selected from a positive connection, a non-positive connection and a combination thereof,
 wherein the plug securing part has a stop structure, wherein the plug securing part comprises, in a region of the stop structure, at least a radial extension in an inserted state perpendicular to a central axis which is at least greater than a minimum but preferably greater than a maximum radial extension of the proximal opening of the base body so that an insertion depth of the plug securing part into the medicament container is limited by abutment of the stop structure against the medicament container, and wherein the stop structure is arranged at an axial distance from a distal end of the plug securing part that is less than or equal to an axial distance between a proximal end of the end plug and the proximal opening of the base body such that the end plug cannot be displaced by the plug securing part.

20. A method of using a plug securing part for securing an end plug in a medicament container, the method comprising:

providing the medicament container, the medicament container including a base body that at least partially surrounds an interior, the base body having a central axis and a proximal opening, wherein the medicament container forms a dual chamber system;

arranging the end plug in the interior such that the end plug is displaceable along the central axis and, the end plug separates a first region of the interior from a second region of the interior, the first region being a distal region of the interior with respect to the end plug, the second region being a proximal region of the interior with respect to the end plug;

inserting the plug securing part at least partially into the second region of the interior through the proximal opening, the plug securing part, when inserted into the interior, being closer to the proximal opening than the end plug, and held, at least in a holding area, in a fixed position in the interior by a connection selected from a positive connection, a non-positive connection and a combination thereof, wherein the plug securing part is inserted into the second region through the proximal opening so that it is positioned closer to the proximal opening than the end plug, wherein the plug securing part is held at least in a holding area of the second region of the medicament container by the positive connection and/or the non-positive connection;

holding the plug securing part onto the base body when inserted into the interior by at least one elastic holding element of the plug securing part, the at least one elastic holding element having an elasticity acting on the central axis at least radially, and subjecting the medicament container to a pressure gradient by a change in altitude and retaining the plug within the medicament container with the plug securing part.

* * * * *